(12) United States Patent
Ishii

(10) Patent No.: US 9,779,207 B2
(45) Date of Patent: Oct. 3, 2017

(54) INFORMATION PROCESSING APPARATUS INFORMATION PROCESSING METHOD, AND STORAGE MEDIUM

(75) Inventor: Masato Ishii, Tokyo (JP)

(73) Assignee: NEC CORPORATION, Tokyo (JP)

( * ) Notice: Subject to any disclaimer, the term of this patent is extended or adjusted under 35 U.S.C. 154(b) by 614 days.

(21) Appl. No.: 13/824,473

(22) PCT Filed: Dec. 19, 2011

(86) PCT No.: PCT/JP2011/079388
§ 371 (c)(1),
(2), (4) Date: May 21, 2013

(87) PCT Pub. No.: WO2012/111235
PCT Pub. Date: Aug. 23, 2012

(65) Prior Publication Data
US 2013/0232140 A1  Sep. 5, 2013

(30) Foreign Application Priority Data
Feb. 17, 2011 (JP) .................................. 2011-031856

(51) Int. Cl.
*G06F 19/24* (2011.01)
*G06K 9/62* (2006.01)
*G06F 17/30* (2006.01)

(52) U.S. Cl.
CPC .............. *G06F 19/24* (2013.01); *G06K 9/623* (2013.01); *G06K 9/6231* (2013.01); *G06F 17/30* (2013.01)

(58) Field of Classification Search
CPC ......... G06T 2207/20081; G06T 7/0081; G06T 7/0087; G06F 19/24; G06F 17/18;
(Continued)

(56) References Cited

U.S. PATENT DOCUMENTS

2009/0028443 A1* 1/2009 Chen .................... G06K 9/6234
382/224
2009/0074292 A1* 3/2009 Rother ................. G06K 9/4638
382/180
(Continued)

FOREIGN PATENT DOCUMENTS

JP 2008-071214 A 3/2008
WO 2007/026130 A1 3/2007

OTHER PUBLICATIONS

A. Krause. "SFO: A Toolbox for Submodular Function Optimization". Journal of Machine Learning Research (2010).*
(Continued)

*Primary Examiner* — Mark D Featherstone
*Assistant Examiner* — Diedra McQuitery
(74) *Attorney, Agent, or Firm* — Sughrue Mion, PLLC

(57) ABSTRACT

An information processing apparatus that selects appropriate features in polynomial time from the viewpoint of both the relevance and the redundancy of features to be selected. This information processing apparatus includes a relevance evaluator that evaluates relevance of each feature included in a set of features, a redundancy evaluator that evaluates redundancy between the features included in the set of features, and a selected feature determiner that determines selected features that optimize a submodular objective function defined using the relevance calculated by the relevance evaluator and the redundancy calculated by the redundancy evaluator.

10 Claims, 12 Drawing Sheets

(58) Field of Classification Search
CPC .. G06F 17/30; G06K 9/0014; G06K 9/00147; G06K 9/6231; G06K 9/623
USPC .................. 382/159, 228; 706/12; 707/723, 707/E17.023
See application file for complete search history.

(56) References Cited

U.S. PATENT DOCUMENTS

| | | | |
|---|---|---|---|
| 2009/0271338 A1* | 10/2009 | Chidlovskii | G06N 99/005 706/12 |
| 2010/0150448 A1* | 6/2010 | Lecerf | G06F 17/3061 382/190 |
| 2012/0088981 A1* | 4/2012 | Liu | G06K 9/6215 600/300 |

OTHER PUBLICATIONS

Boukouvalas, Alexis, Dan Cornford, and Milan Stehlik. "Approximately optimal experimental design for heteroscedastic Gaussian process models." (2009).*

Yoshinobu Kawahara, et al.,"Submodularity Cuts and Applications", Technical Reports on Information-Based Induction Sciences (IBIS 2009), Oct. 19-21, 2009, pp. 1-9.

Hanchuan Peng, et al., "Feature Selection Based on Mutual Information: Criteria of Max-Dependency, Max-Relevance, and Min-Redundancy", IEEE Transactions on Pattern Analysis and Machine Intelligence, Aug. 2005, pp. 1226-1238, vol. 27, No. 8.

Kiyohito Nagano, et al., "Submodular Optimization Approaches to Machine Learning", The 22nd Workshop on Circuits and Systems in Karuizawa, Apr. 20-21, 2009, pp. 231-236.

Luping Zhou, et al., "Feature Selection with Redundancy-Constrained Class Separability", IEEE Transactions on Neural Networks, May 2010, pp. 853-858, vol. 21, No. 5.

Steven Loscalzo, "Consensus Group Stable Feature Selection", ACM SIGKDD International Conference on Knowledge Discovery and Data Mining, Jun. 28-Jul. 1, 2009, pp. 567-576.

Isabelle Guyon, et al., "An Introduction to Variable and Feature Selection", the Journal of Machine Learning Research, 2003, pp. 1157-1182, vol. 3.

Vladimir Kolmogorov, et al., "What Energy Functions Can Be Minimized via Graph Cuts?", IEEE Transactions on Pattern Analysis and Machine Intelligence, Feb. 2004, pp. 147-159, vol. 26, No. 2.

* cited by examiner

INFORMATION PROCESSING APPARATUS INFORMATION PROCESSING METHOD, AND STORAGE MEDIUM

CROSS REFERENCE TO RELATED APPLICATIONS

This application is a National Stage of International Application No. PCT/JP2011/079388 filed Dec. 19, 2011, claiming priority based on Japanese Patent Application No. 2011-031856, filed Feb. 17, 2011, the contents of all of which are incorporated herein by reference in their entirety.

TECHNICAL FIELD

The present invention relates to a technique of selecting a set of features effective for pattern recognition or the like.

BACKGROUND ART

Patent literatures 1 and 2 disclose, as a kind of feature selection technique of selecting some features to be used in machine learning or the like from an input set of features, a technique focusing the relevance of features to reduce the calculation cost of learning/identification or the like. However, since all feature combinations are directly evaluated, the calculation cost of feature candidate search is high, and appropriate feature selection cannot be done in polynomial time.

On the other hand, non-patent literatures 1, 2, and 3 disclose a method of efficiently selecting features by evaluating the redundancy between features (in other words, low redundancy) in addition to the relevance of features.

CITATION LIST

Patent Literature

Patent literature 1: WO 2007/026130
Patent literature 2: Japanese Patent Laid-Open No. 2008-071214

Non-Patent Literature

Non-patent literature 1: L. Zhou, L. Wang, and C. Shen, "Feature Selection with Redundancy-Constrained Class Separability", IEEE Transaction on Neural Networks, Vol. 21, No. 5, pp. 853-858, 2010
Non-patent literature 2: S. Loscalzo, L. Yu, and C. Ding, "Consensus Group Stable Feature Selection", ACM SIGKDD International Conference on Knowledge Discovery and Data Mining, pp. 567-576, 2009
Non-patent literature 3: H. Peng, F. Long, C. Ding, "Feature Selection Based on Mutual Information: Criteria of Max-Dependency, Max-Relevance, and Min-Redundancy", IEEE Transactions on Pattern Analysis and Machine Intelligence, Vol. 27, no. 8, pp. 1226-1238, 2005

SUMMARY OF THE INVENTION

Technical Problem

In non-patent literatures 1 and 2, however, an input set of features is first clustered in accordance with the redundancy between features. Next, feature selection is performed using the relevance of features under a constraint using the clustering result. That is, since optimization by relevance and optimization by redundancy are separately performed, the technique does not guarantee obtaining truly appropriate feature selection from the viewpoint of both the relevance and the redundancy.

In non-patent literature 3, when selecting features one by one in consideration of the relevance, redundancy from other features is taken into consideration. For this reason, the technique does not guarantee that the final feature combination is appropriate. If the feature selected first is inappropriate, the final feature combination cannot be appropriate.

The present invention enables to provide a technique of solving the above-described problem.

Solution to Problem

One aspect of the present invention provides an information processing apparatus comprising:
a relevance evaluator that evaluates relevance of each feature included in a set of features;
a redundancy evaluator that evaluates redundancy between the features included in the set of features; and
a selected feature determiner that determines selected features that optimize a submodular objective function defined using the relevance calculated by the relevance evaluator and the redundancy calculated by the redundancy evaluator.

Another aspect of the present invention provides an information processing method comprising:
evaluating relevance of each feature included in a set of features;
evaluating redundancy between the features included in the set of features; and
determining selected features that optimize a submodular objective function defined using the relevance calculated in the evaluating the relevance and the redundancy calculated in the evaluating the redundancy.

Still other aspect of the present invention provides a non-transitory computer-readable storage medium storing a program that causes a computer to execute:
evaluating relevance of each feature included in a set of features;
evaluating redundancy between the features included in the set of features; and
determining selected features that optimize a submodular objective function defined using the relevance calculated in the evaluating the relevance and the redundancy calculated in the evaluating the redundancy.

Advantageous Effects of Invention

According to the present invention, it is possible to select appropriate features in polynomial time from the viewpoint of both the relevance and the redundancy of features to be selected.

DESCRIPTION OF THE EMBODIMENTS

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
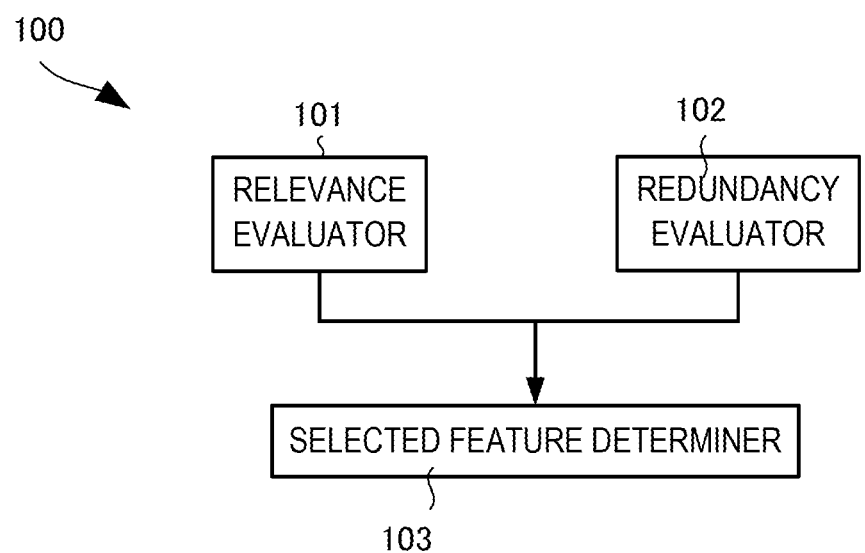
FIG. 1 is a block diagram showing the arrangement of an information processing apparatus according to the first embodiment of the present invention.

An information processing apparatus 100 according to the first embodiment of the present invention will be described with reference to FIG. 1. The information processing apparatus 100 includes a relevance evaluator 101, a redundancy evaluator 102, and a selected feature determiner 103. The information processing apparatus 100 determines a plurality of features to be selected from a set of features.

The relevance evaluator 101 evaluates the relevance of each features included in the set of features. The redundancy evaluator 102 evaluates the redundancy between the features included in the set of features. The selected feature determiner 103 determines selected features that optimize a submodular objective function defined using the relevance calculated by the relevance evaluator 101 and the redundancy calculated by the redundancy evaluator 102.

The above-described arrangement allows to select appropriate features in polynomial time from the viewpoint of both the relevance and the redundancy of features to be selected.

Second Embodiment

An information processing apparatus 200 according to the second embodiment of the present invention will be described next with reference to FIG. 2 and subsequent drawings. In the information processing apparatus 200, an objective function E is defined using both the relevance of each feature and the redundancy between features. The objective function E is designed to have a small value when selecting a set of features having high relevance and low redundancy. In addition, the objective function E is defined as a function meeting submodularity, and an optimization method such as graph cut is used, thereby performing global optimization.

[Prerequisite Technique]

Figure 10:
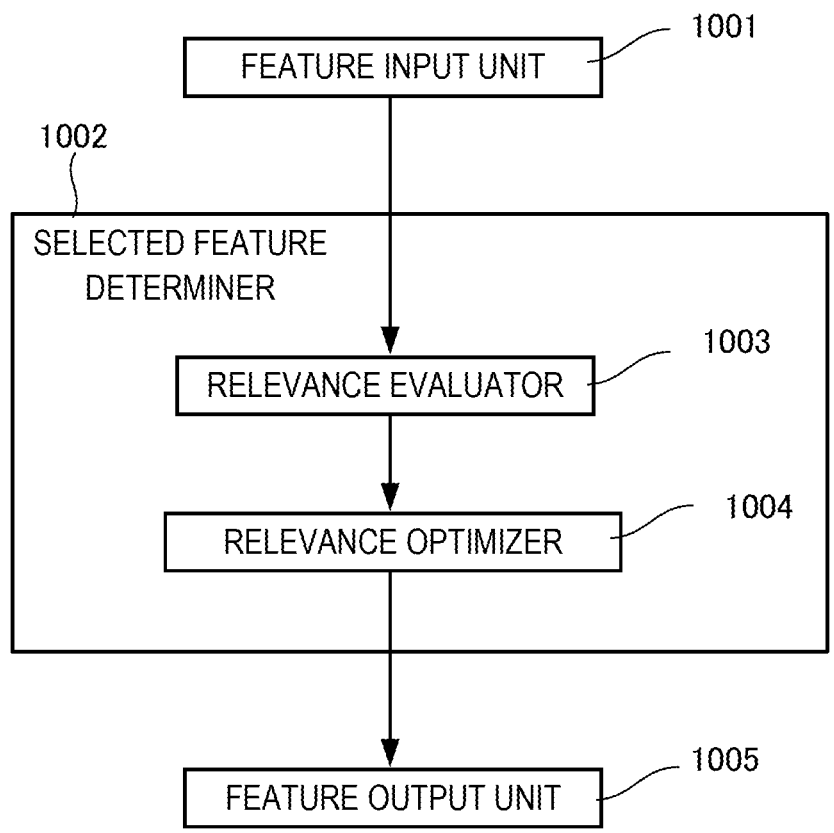
FIG. 10 is a view for explaining a prerequisite technique according to the second embodiment of the present invention.

A technique that is a prerequisite of the feature selection method applied in the information processing apparatus 200 according to this embodiment will be described first. When determining a feature to be selected from a set of features including a plurality of features, the relevance of each feature may be evaluated based on some criterion, and the features may be selected in descending order of relevance. FIG. 10 is a view showing the system arrangement in that case. A selected feature determiner 1002 determines a set of features to be selected from a plurality of features input by a feature input unit 1001. A feature output unit 1005 outputs the set of features to be selected. In the selected feature determiner 1002, a relevance evaluator 1003 evaluates relevance. A relevance optimizer 1004 selects a feature that optimizes the relevance of each feature. The relevance represents how much a feature is relevant at the time of machine learning. A Fisher score or correlation between a feature and a class can be used as the relevance.

Figure 11:
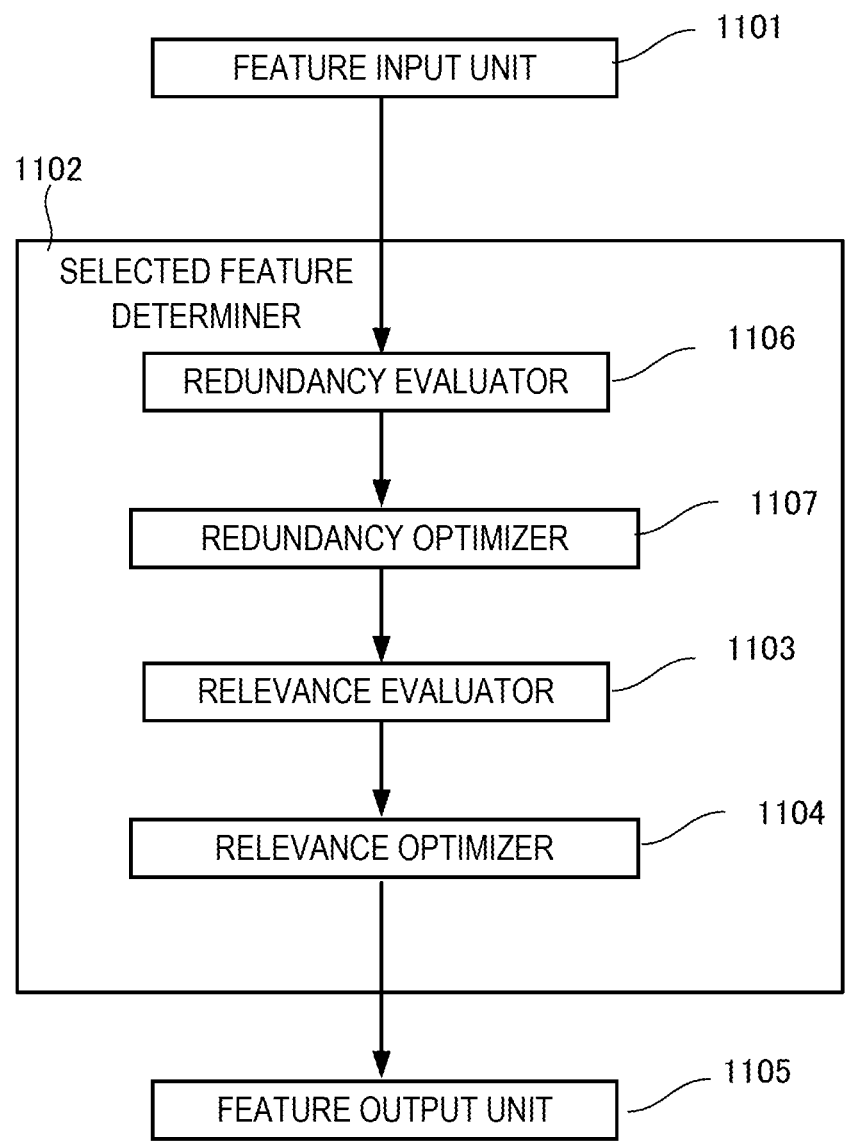
FIG. 11 is a view for explaining another prerequisite technique according to the second embodiment of the present invention.

In the arrangement shown in FIG. 10, however, if features that are highly relevant but redundant to each other are included in the input set of features (in an extreme case, a plurality of identical features are included), the features redundant to each other are included in the selected features. To avoid this problem, the redundancy between features may be evaluated as well as the relevance of each feature, as shown in FIG. 11. The redundancy is taken into consideration. The redundancy represents how much a plurality of features are redundant to each other. Examples of widely used redundancy are a coefficient of correlation and mutual information. In the arrangement shown in FIG. 11, a selected feature determiner 1102 determines a set of features to be selected from a plurality of features input by a feature input unit 1101. A feature output unit 1105 outputs the set of features to be selected. In the selected feature determiner 1102, a redundancy evaluator 1106 evaluates the redundancy. After that, a redundancy optimizer 1107 optimizes the redundancy. A relevance evaluator 1103 evaluates relevance. A relevance optimizer 1104 selects a feature that optimizes the relevance of each feature. That is, an input set of features is clustered in accordance with the redundancy between features. Next, feature selection is performed using the relevance of features under a constraint using the clustering result.

However, since optimization by relevance and optimization by redundancy are separately performed, this method does not guarantee obtaining optimum feature selection from the viewpoint of both the relevance and the redundancy.

Figure 12:
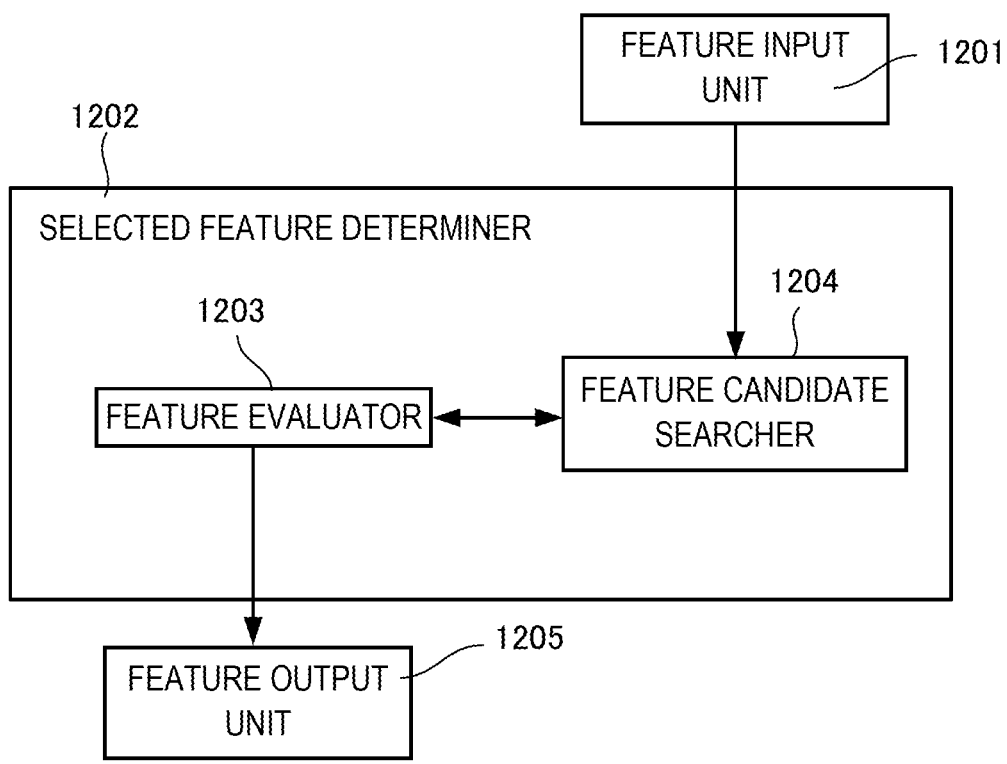
FIG. 12 is a view for explaining still another prerequisite technique according to the second embodiment of the present invention.

In an arrangement shown in FIG. 12, a selected feature determiner 1202 determines a set of features to be selected from a plurality of features input by a feature input unit 1201. A feature output unit 1205 outputs the set of features to be selected. In the selected feature determiner 1202, a feature candidate search by a feature candidate searcher 1204 and feature candidate evaluation by a feature evaluator 1203 are repeated to find an optimum set of features. In this method, since the feature combination is directly evaluated, more accurate feature selection can be done. On the other hand, the calculation cost of the feature candidate search is high, and no optimum feature selection can be obtained in polynomial time.

Eventually, the arrangements shown in FIGS. 10 to 12 cannot obtain truly optimum feature selection from the viewpoint of both the relevance and the redundancy of the set of features to be selected. This is because the stage of evaluating the relevance of a feature and the stage of evaluating the redundancy between features are connected in series, and the optimization is separately performed, or because the features are selected one by one, and the optimization is performed for the finally selected set of features.

Figure 7:
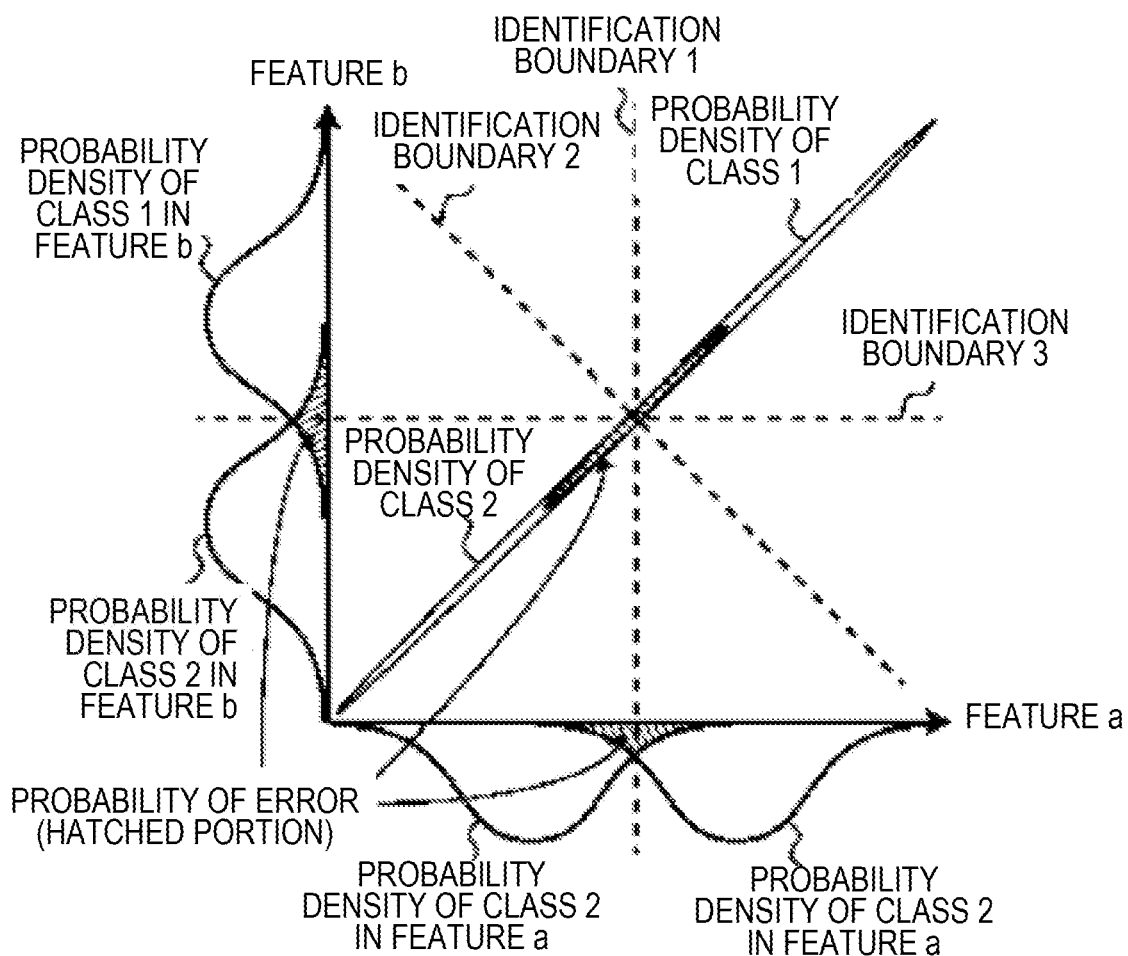
FIG. 7 is a view for explaining a prerequisite technique according to the second embodiment of the present invention.

For example, assume that two features are selected in a data set concerning a two-class identification problem. In the identification problem, the relevance of a feature can be expressed as the lowness of the probability of error by an optimum identification boundary when only the feature is used. This equals the smallness of the area of the overlap portion of the probability density functions of samples in each class. FIG. 7 shows probability density functions concerning the sample distribution of each class when features a and b having equal relevance and very high correlation are selected. Since the two features have very high correlation, the samples are distributed on a=b. For this reason, the three types of identification boundaries shown in FIG. 7 exhibit the same performance. The probability of error (the area of the hatched portion in FIG. 7) is the same as in a case in which only one of the features is used. On the other hand, assume a case in which a feature c that is less relevant but has almost no correlation with the feature a is selected in place of the feature b.

Figure 8:
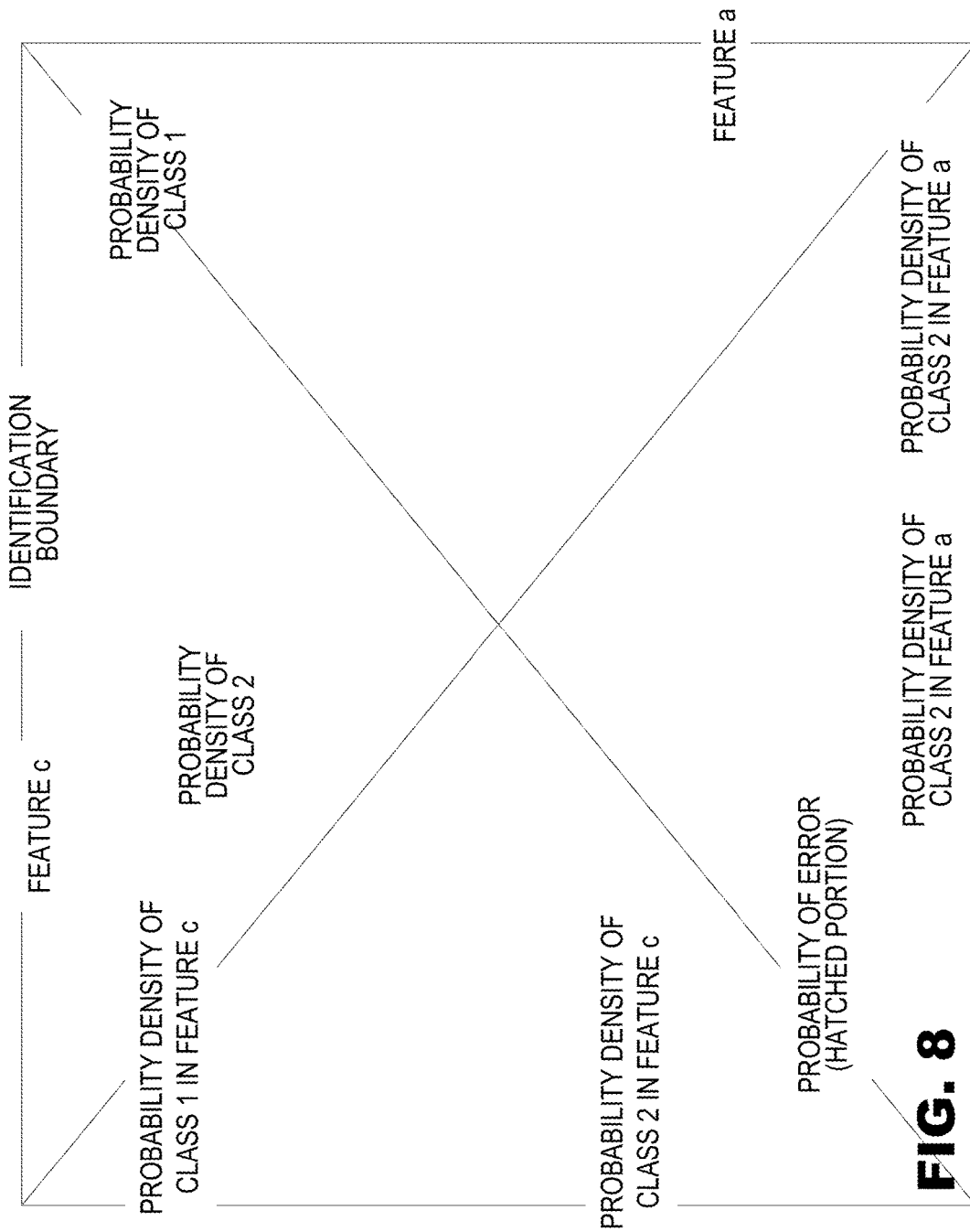
FIG. 8 is a view for explaining a prerequisite technique according to the second embodiment of the present invention.
Figure 9:
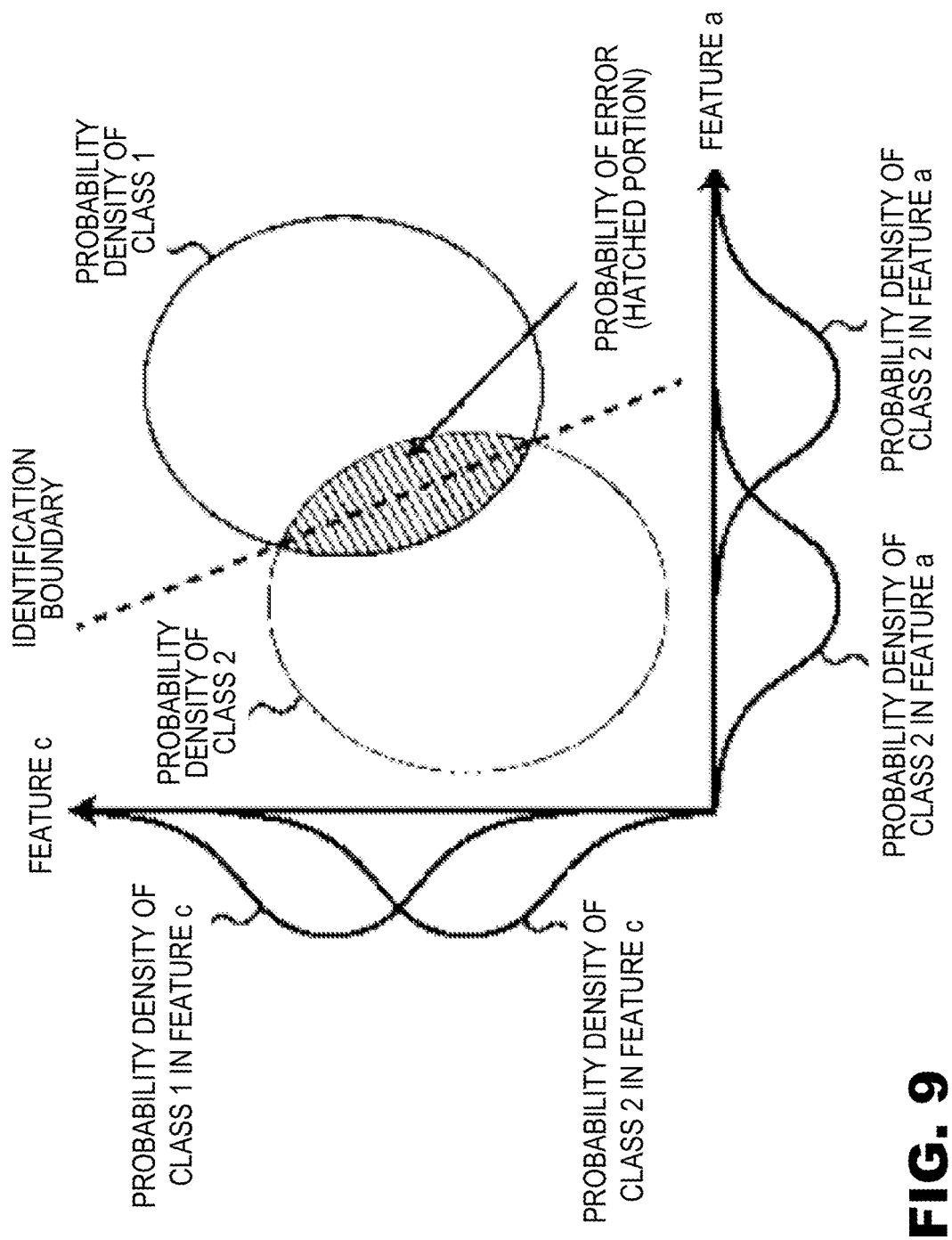
FIG. 9 is a view for explaining a prerequisite technique according to the second embodiment of the present invention.

At this time, an identification boundary as shown in FIG. 8 exhibits the same probability of error as that when only the feature a is used. When the features a and b are used, this identification boundary is optimum. However, when the features a and c are used, an identification boundary of a lower probability of error exists, as shown in FIG. 9. That is, selecting the feature c that is less relevant but has no correlation is more preferable than selecting the feature b having very high correlation. As is apparent from the above-described example, the relevance of each feature and the redundancy between features need to be simultaneously taken into consideration in feature selection.

[Explanation of Functional Arrangement]

Figure 2:
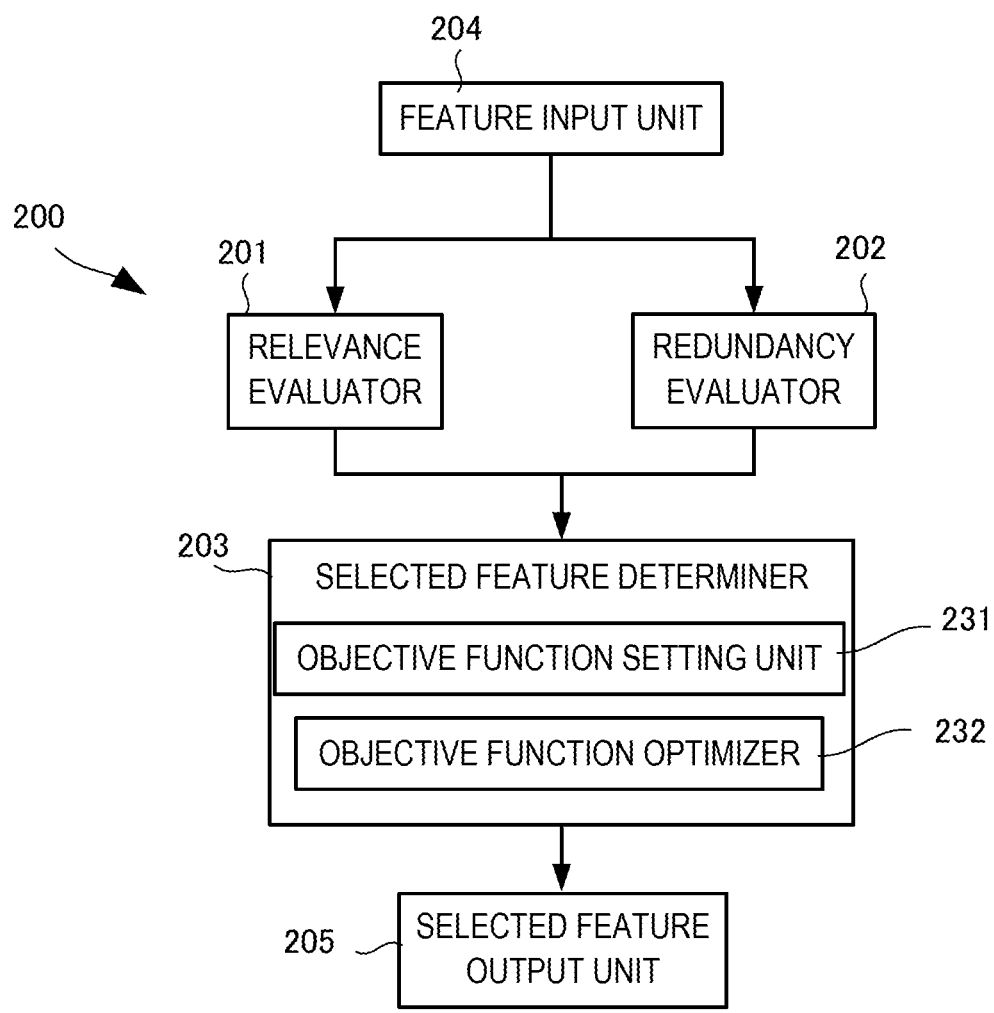
FIG. 2 is a block diagram showing the functional arrangement of an information processing apparatus according to the second embodiment of the present invention.

FIG. 2 is a block diagram showing the functional arrangement of the information processing apparatus 200 according to this embodiment. The information processing apparatus 200 includes a feature input unit 204 that inputs a set of features extracted in advance, a relevance evaluator 201 that evaluates the relevance of each input feature, and a redundancy evaluator 202 that evaluates the redundancy of each input feature. The information processing apparatus 200 also includes a selected feature determiner 203 that determines, based on the evaluation results of the relevance and redundancy, a set of features to be selected, and a selected feature output unit 205 that outputs the determined set of features to be selected.

The relevance evaluator 201 calculates relevance using a predetermined method for each feature as relevance in learning. For example, relevance using two or more features as arguments is calculated. The redundancy evaluator 202 calculates redundancy using a predetermined method as redundancy between features. For example, redundancy is calculated from two features extracted from the set of features. Redundancy using three or more features as arguments may be calculated.

An objective function setting unit 231 sets a submodular objective function using the relevance of the features obtained by the relevance evaluator 201 and the redundancy between the features obtained by the redundancy evaluator 202. An objective function optimizer 232 optimizes the constructed submodular objective function.

[Explanation of Hardware Arrangement]

Figure 3:
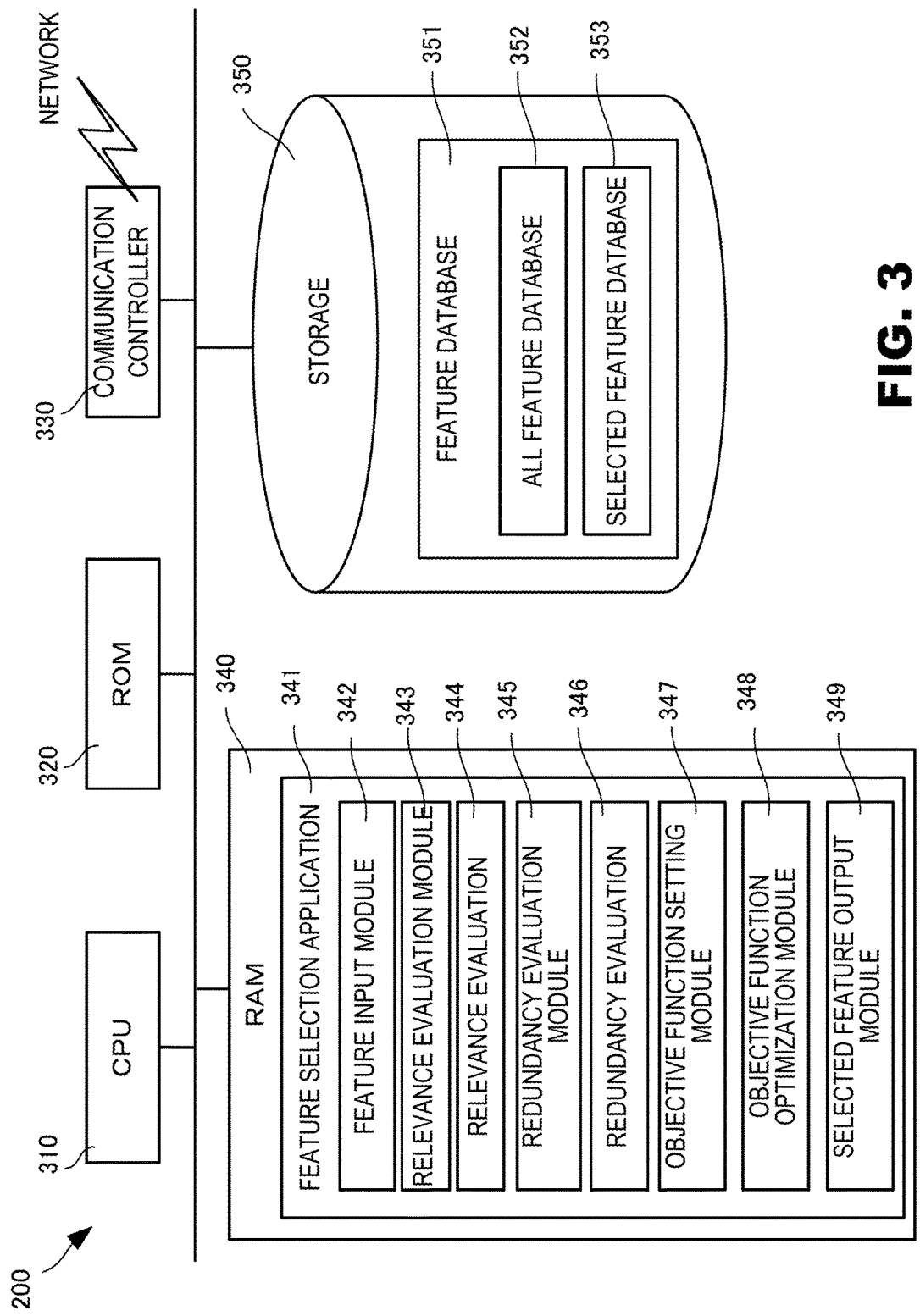
FIG. 3 is a block diagram showing the hardware arrangement of the information processing apparatus according to the second embodiment of the present invention.

FIG. 3 is a block diagram showing the hardware arrangement of the information processing apparatus 200 according to this embodiment. The information processing apparatus 200 includes a CPU 310, a ROM 320, a communication controller 330, a RAM 340, and a storage 350. The CPU 310 is a central processing unit and controls the entire information processing apparatus 200 by executing various programs. The ROM 320 is a read only memory and stores the boot program to be executed first by the CPU 310 and various kinds of parameters. The communication controller 330 controls communication with another terminal via a network.

The RAM 340 is a random access memory and includes an area to execute a feature selection application 341. The feature selection application 341 includes a feature input module 342, a relevance evaluation module 343, a redundancy evaluation module 345, and an objective function setting module 347. On the other hand, the storage 350 includes an all feature database 352 and a selected feature database 353 as a feature database 351.

[Explanation of Operation]

Figure 4:
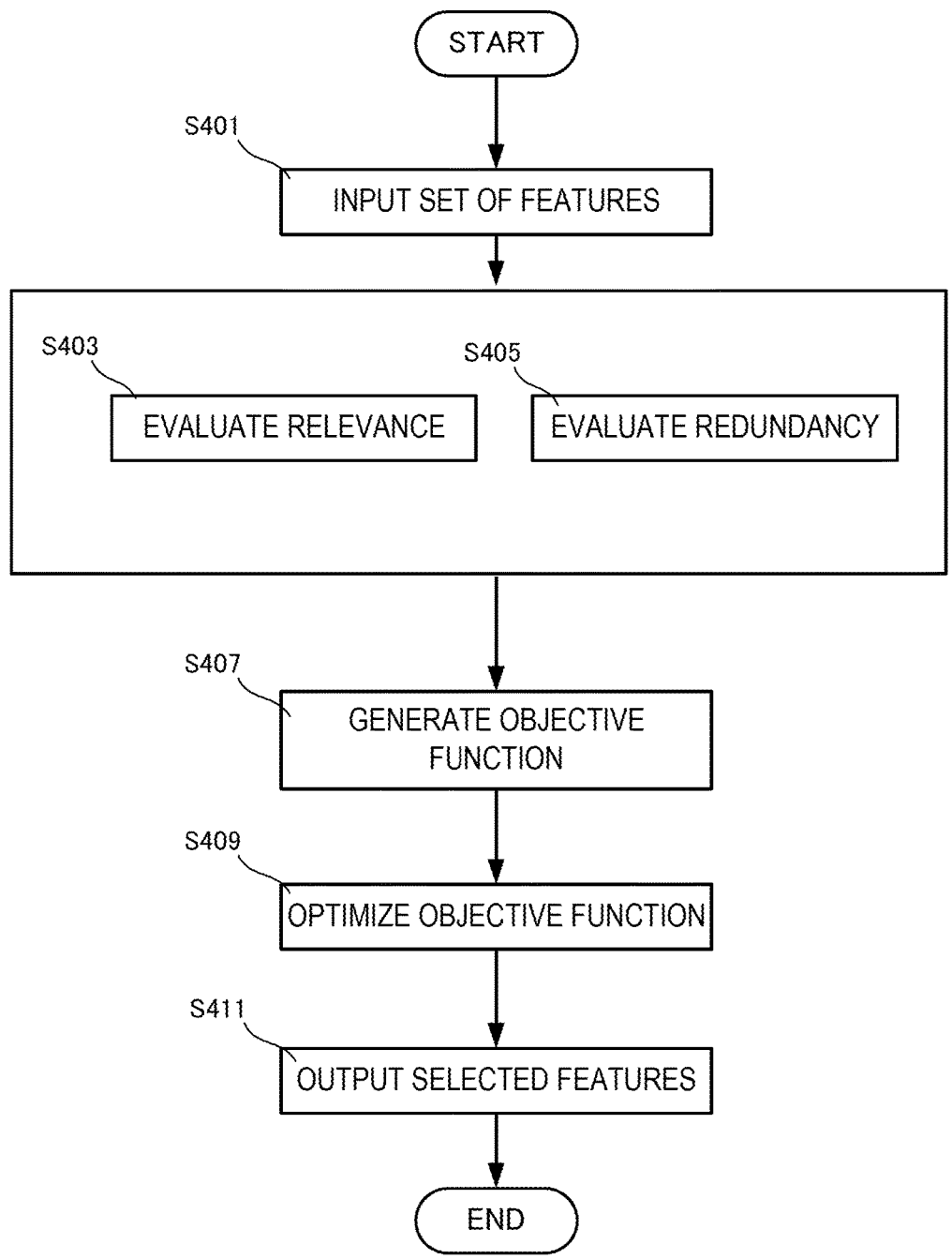
FIG. 4 is a flowchart showing the procedure of processing of the information processing apparatus according to the second embodiment of the present invention.

An operation according to this embodiment will be described in detail with reference to FIGS. 2 to 4. FIG. 4 is a flowchart showing the procedure of processing of the information processing apparatus according to this embodiment.

In step S401, the CPU 310 functions as the feature input unit 204 by executing the feature input module 342 and receives input of a set of features extracted in advance for machine learning.

Next, the CPU 310 functions as the relevance evaluator 201 by executing the relevance evaluation module 343 and evaluates the relevance of each of the plurality of input features. The CPU temporarily stores a generated relevance evaluation 344 in the RAM 340 and outputs it to the selected feature determiner 203 (step S403).

Almost simultaneously, the CPU 310 functions as the redundancy evaluator 202 by executing the redundancy evaluation module 345 and evaluates the redundancy of each of the plurality of input features. The CPU temporarily stores a generated redundancy evaluation 346 in the RAM 340 and outputs it to the selected feature determiner 203 (step S403).

The CPU 310 functions as the objective function setting unit 231 by executing the objective function setting module 347 and generates a submodular objective function using the input relevance and redundancy (step S409).

The CPU 310 functions as the objective function optimizer 232 by executing an objective function optimization module 348 and optimizes the objective function generated in step S409. The selected feature output unit 205 determines, based on the objective function optimization result, the set of features to be selected and outputs the set of features (step S411).

[Procedure of Processing Using Equations]

A feature evaluation method will be described in detail by exemplifying the identification problem. N samples each including d features and N class levels representing classes to which the respective samples belong are assumed as input. A matrix in which the samples are arranged will be represented by X, and a vector in which the class levels are arranged will be represented by y hereinafter. Feature selection is processing of determining selection or non-selection of the d features and can be defined as processing of determining a vector s given by
[Mathematical 1]

$$s=(s_1,s_2,\ldots,s_d)^T \qquad (1)$$

where each element of s takes a value 0 (selection) or 1 (non-selection)

Using the input sample X and class level y, the relevance evaluator 201 calculates relevance E1 of each of the d features by
[Mathematical 2]

$$E_1(s_i,X^{(i)},y) \qquad (2)$$

where $X^{(i)}$ is the sample group including only the ith feature. The relevance E1 can be defined using, for example, the coefficient of correlation between each feature and a class level or the identification performance of an identifier that has learned using only one feature (Guyon and A. Elisseeff, "An Introduction to Variable and Feature Selection," the Journal of Machine Learning Research, vol. 3, pp. 1157-1182, 2003).

The redundancy evaluator 202 calculates redundancy E2 for all feature combinations using
[Mathematical 3]

$$E_2(s_i,s_j,X^{(i)},X^{(j)},y) \qquad (3)$$

However, the redundancy E2 is defined to always meet a condition called submodularity represented by
[Mathematical 4]

$$E_2(0,0,X^{(i)},X^{(j)},y)+E_2(1,1,X^{(i)},X^{(j)},y) \leq E_2(0,1,X^{(i)}, X^{(j)},y)+E_2(1,0,X^{(i)},X^{(j)},y) \qquad (4)$$

The submodularity is described in V. Kolmogorov and R. Zabih, "What Energy Functions Can Be Minimized via Graph Cuts?", IEEE Transactions on Pattern Analysis and Machine Intelligence, vol. 26, no. 2, pp. 147-159, 2004. The redundancy E2 can be defined using, for example, the coefficient of correlation between the features or the mutual information.

Using the relevance E1 and the redundancy E2, the objective function setting unit 231 minimizes the objective function E by

[Mathematical 5]

$$E(s) = -\sum_i E_1(s_i, X^{(i)}, y) + \lambda \sum_{i,j} E_2(s_i, s_j, X^{(i)}, X^{(j)}, y) \qquad (5)$$

where λ is a positive constant that determines the relative weight of two terms.

To minimize the objective function E, for example, a method such as graph cut can be used. More specifically, a submodular objective function including terms using two features as arguments at maximum is optimized here to determine selected features. The selected feature output unit 205 receives the feature selection vector s output from the objective function optimizer 232 and outputs a set X' of features that minimize the objective function E.
[Mathematical 6]

$$X'=\{X^{(i)}|i:s_i=1\} \qquad (6)$$

As the optimization method, any submodular objective function minimization method such as graph cut or ellipsoid method can be used. Note that in this case, the relevance E1 is calculated from only each feature, and the redundancy E2 is calculated from only two features. However, a term of relevance using two or more features as arguments or a term of redundancy using three or more features as arguments can also be defined generally within the range where the objective function E meets the submodularity. For example, when calculating relevance using m or less features and redundancy using n or less features, the objective function E is given by

[Mathematical 7]

$$E(s) = -\sum_i E_1(s_{i(1)},\ldots,s_{i(m)}, X, y) + \lambda \sum_j (s_{j(1)},\ldots,s_{j(n)}, X, y) \qquad (7)$$

where $i(1),\ldots,i(m)$ and $j(1),\ldots,j(n)$ are indices of features when m features and n features are selected, respectively.

At this time, the necessary and sufficient condition to cause the objective function E to meet the submodularity is to meet inequality (4) described above, and both E1 and E2 need to be designed carefully.

Detailed Example

Figure 5:
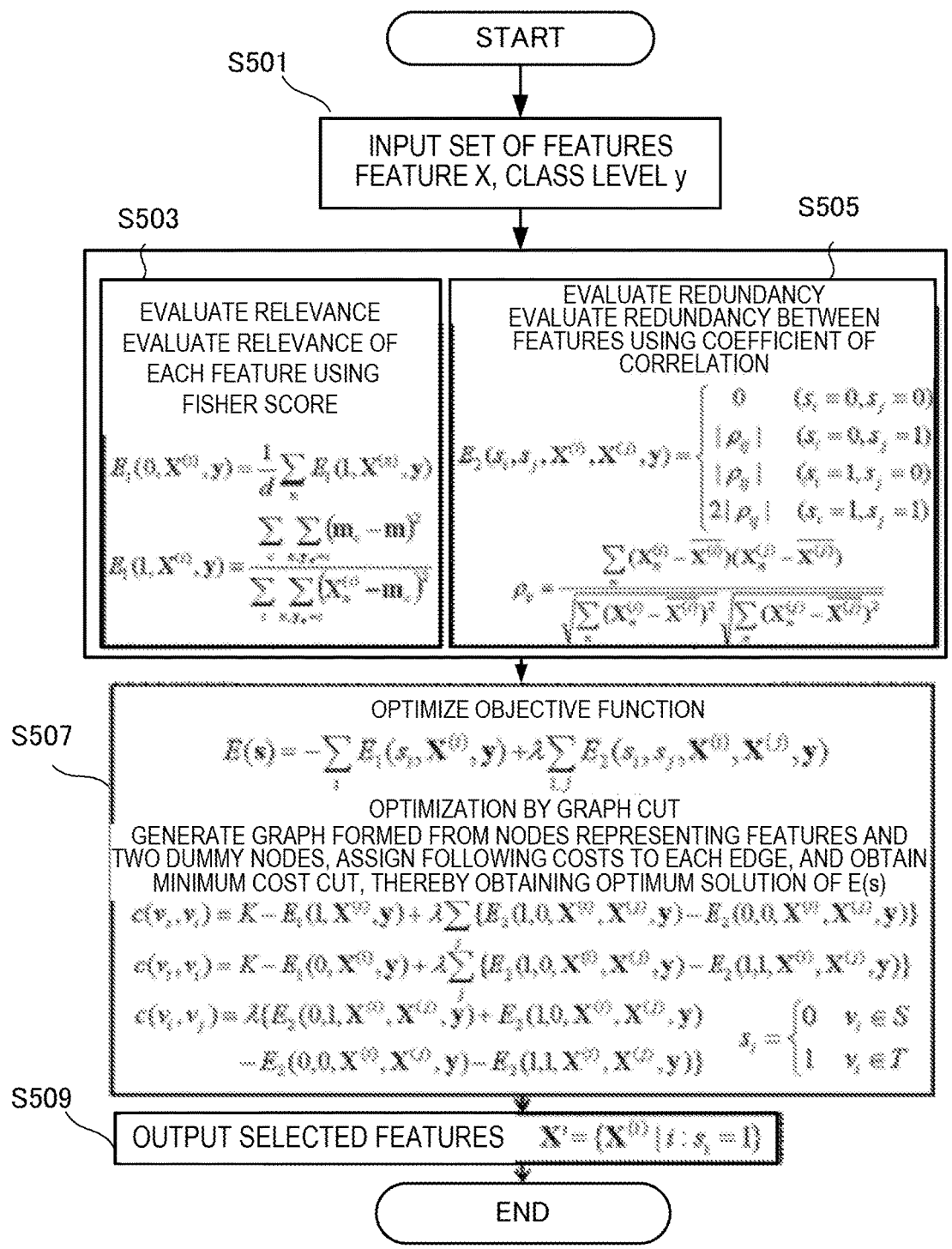
FIG. 5 is a flowchart showing a detailed example of the procedure of processing of the information processing apparatus according to the second embodiment of the present invention.

A detailed example will be described with reference to the flowchart of FIG. 5. In step S501, the feature input unit 204 inputs the samples X and y. The relevance evaluator 201 calculates the relevance E1 using a Fisher score by

[Mathematical 8]

$$E_1(1, X^{(i)}, y) = \frac{\sum_c n_c(m_c^{(i)} - m^{(i)})^2}{\sum_c \sum_{n,y_n=c} (X_n^{(i)} - m_c^{(i)})^2} \qquad (8)$$

where m is the average of all samples, mc is the average of samples belonging to a class c, and nc is the number of samples belonging to the class c (step S503).

Equation (8) indicates a scale called a Fisher score and generally represents that the larger the value is, the higher the separation of samples of each class is, and the easier the identification is. As for E1, to select a relevant feature by minimizing the objective function E, the higher the relevance of a feature is, the larger E1(1, X, y) for E1(0, X, y) needs to be. E1(0, X, y) can be defined by several methods which can roughly be divided into two types of designs. One method uses an appropriate constant value (for example, equation (9)), and the other uses a value depending on E1 (1, X, y) (for example, equation (10)).
[Mathematical 9]

$$E_1(0,X^{(i)},y)=\theta \qquad (9)$$

[Mathematical 10]

$$E_1(0,X^{(i)},y)=\theta-E_1(1,X^{(i)},y) \qquad (10)$$

where θ is a constant and can use, for example, an average of E1 (1, X, y), like

[Mathematical 11]

$$\theta = \frac{1}{d} E_1(1, X^{(i)}, y) \qquad (11)$$

The redundancy evaluator 202 calculates the redundancy E2 using a coefficient ρ of correlation by

[Mathematical 12]

$$E_2(s_i, s_j, X^{(i)}, X^{(j)}, y) = \begin{cases} a_{00} \, |\rho_{ij}| \, (s_i = 0, s_j = 0) \\ a_{01} \, |\rho_{ij}| \, (s_i = 0, s_j = 1) \\ a_{10} \, |\rho_{ij}| \, (s_i = 1, s_j = 0) \\ a_{11} \, |\rho_{ij}| \, (s_i = 1, s_j = 1) \end{cases} \qquad (12)$$

where $a_{00} + a_{11} \leq a_{01} + a_{10}$

[Mathematical 13]

$$\rho_{ij} = \frac{\sum_n (X_n^{(i)} - \overline{X^{(i)}})(X_n^{(j)} - \overline{X^{(j)}})}{\sqrt{\sum_n (X_n^{(i)} - \overline{X^{(i)}})^2} \sqrt{\sum_n (X_n^{(j)} - \overline{X^{(j)}})^2}} \qquad (13)$$

(step S505). In equation (12), a00, a01, a10, and a11 are constants and are set by

[Mathematical 14]

$$a_{00}=0, a_{01}=1, a_{10}=1, a_{11}=2 \qquad (14)$$

The absolute value of the coefficient ρij of correlation represents a high redundancy between the ith feature and the jth feature.

E2 defined in the above-described way has a small value for features having a low correlation, and selection/non-selection is determined mainly by the relevance E1. On the other hand, features having a high correlation are hardly selected simultaneously because E2 has a large energy when selecting both. This allows to easily select features having a high relevance and a low redundancy. In addition, E2 meets the submodularity (inequality (4)).

Ideally, a minimum necessary number of features are selected. For this reason, a00, a01, a10, and a11 are preferably set such that E2 becomes large as the number of selected features is large. The constants a00, a01, a10, and a11 can freely be set within the range to meet the submodularity. The constants a01 and a10 need not always match. For example, the constants a01 and a10 may be set such that the value of E2 becomes small when selecting only relevant features. The objective function optimizer 232 optimizes the objective function E formed from E1 and E2 defined in the above-described way by graph cut (step S507). Details of the optimization using graph cut are described in V. Kolmogorov and R. Zabih, "What Energy Functions Can Be Minimized via Graph Cuts?", IEEE Transactions on Pattern Analysis and Machine Intelligence, vol. 26, no. 2, pp. 147-159, 2004.

Figure 6:
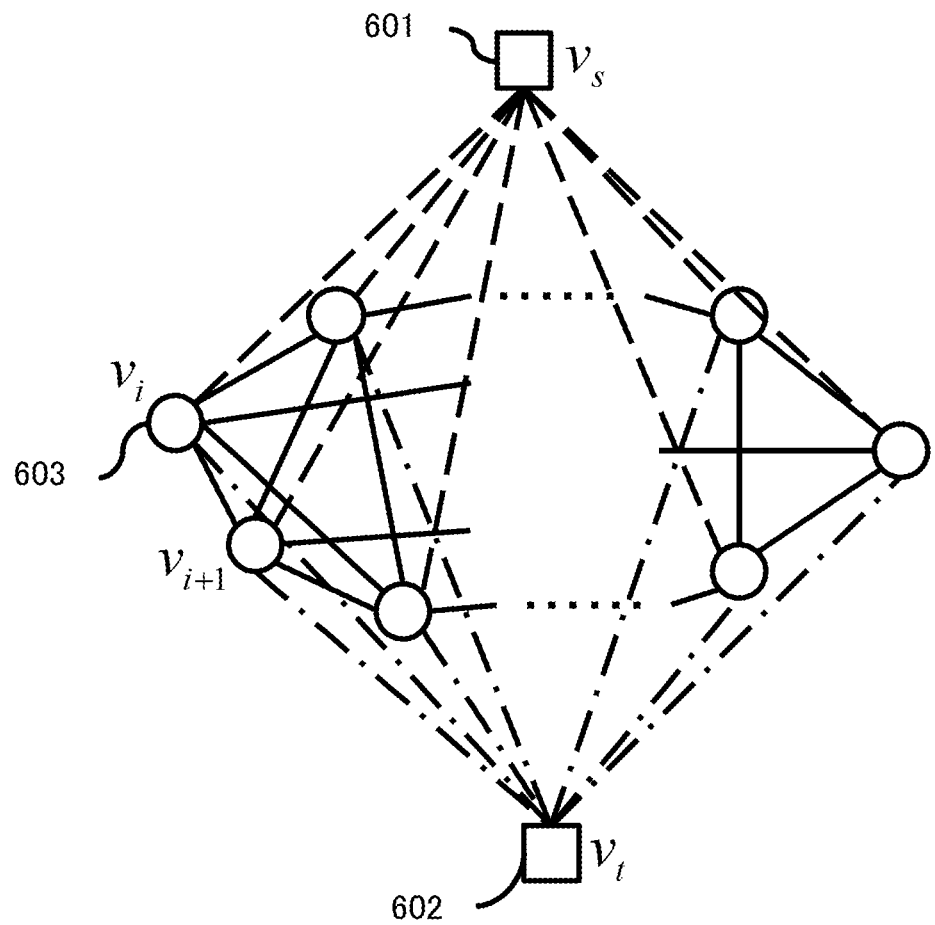
FIG. 6 is a view for explaining graph cut of the information processing apparatus according to the second embodiment of the present invention.

Optimization by graph cut will be described. As shown in FIG. 6, a graph formed from d nodes vi (603) representing the features and two dummy nodes vs and vt (601 and 602) is generated first. All nodes are connected by edges. A cost c is assigned to each edge by

[Mathematical 15]

$$c(v_s, v_i) = K - E_1(1, X^{(i)}, y) + \qquad (15)$$
$$\lambda \sum_j \{E_2(1, 0, X^{(i)}, X^{(j)}, y) - E_2(0, 0, X^{(i)}, X^{(j)}, y)\}$$

[Mathematical 16]

$$c(v_t, v_i) = K - E_1(0, X^{(i)}, y) + \qquad (16)$$
$$\lambda \sum_j \{E_2(0, 1, X^{(i)}, X^{(j)}, y) - E_2(1, 1, X^{(i)}, X^{(j)}, y)\}$$

[Mathematical 17]

$$c(v_i, v_j) = \lambda \{E_2(0, 1, X^{(i)}, X^{(j)}, y) + E_2(1, 0, X^{(i)}, X^{(j)}, y) - \qquad (17)$$
$$E_2(0, 0, X^{(i)}, X^{(j)}, y) - E_2(1, 1, X^{(i)}, X^{(j)}, y)\}$$

where K is a sufficiently large constant set not to make the edge cost negative.

The graph generated in the above-described way is cut between vs and vt and divided into a set S of nodes including vs and a set T of nodes including vt. At this time, cut of minimum cost is obtained using graph cut, and s is determined by

[Mathematical 18]

$$s_i = \begin{cases} 0 & v_i \in S \\ 1 & v_i \in T \end{cases} \qquad (18)$$

In this case, s matches the global optimum solution of the objective function E. This is proved in V. Kolmogorov and R. Zabih, "What Energy Functions Can Be Minimized via Graph Cuts?", IEEE Transactions on Pattern Analysis and Machine Intelligence, vol. 26, no. 2, pp. 147-159, 2004.

For the ith feature, if si=1 in the solution s obtained by graph cut, the selected feature output unit 205 selects the feature. If si=0, the selected feature output unit 205 does not select the feature. The set of features to be finally selected is thus determined.

In this case, graph cut is used to minimize the objective function E. In general, there exist a plurality of methods of minimizing the submodular objective function in polynomial time, and the objective function optimizer 232 can also use these methods. Note that each feature included in the set of features may include a plurality of parameters.

Effects of Embodiment

According to this embodiment, it is possible to obtain optimum feature selection from the viewpoint of both the relevance and the redundancy of a set of features. This is because an objective function including a term for evaluating the relevance of a feature and a term for evaluating the redundancy between features is used.

It is also possible to obtain truly optimum feature selection in polynomial time. The polynomial time indicates that the calculation time increases only by a constant power of the number of input features. This is because feature selection is done as minimization of the objective function meeting the submodularity.

INDUSTRIAL APPLICABILITY

The above-described embodiments are applicable as preprocessing of learning for application purposes such as face recognition, object recognition, character recognition, and speech recognition.

Other Embodiments

The present invention has been described above with reference to the embodiments. However, the present invention is not limited to those embodiments. Various changes and modifications understandable by those skilled in the art within the scope of the present invention can be made for the arrangements and details of the present invention. The present invention also incorporates a system or apparatus that somehow combines different features included in the respective embodiments.

The present invention is applicable to a system including a plurality of devices or a single apparatus. The present invention is also applicable even when a program for implementing the functions of the embodiments is supplied to the system or apparatus directly or from a remote site. Hence, the present invention also incorporates the program installed in a computer to implement the functions of the present invention on the computer, a storage medium storing the program, and a WWW (World Wide Web) server that causes a user to download the program.

Other Expressions of Embodiments

Some or all of the above-described embodiments can also be described as in the following supplementary notes but are not limited to the followings.

(Supplementary Note 1)

There is provided an information processing apparatus comprising:

a relevance evaluator that evaluates relevance by calculating relevance of each feature included in a set of features;

a redundancy evaluator that evaluates redundancy by calculating redundancy between the features included in the set of features; and a selected feature determiner that determines selected features such that a submodular objective function defined using the relevance calculated by the relevance evaluator and the redundancy calculated by the redundancy evaluator meets a predetermined condition.

(Supplementary Note 2)

There is provided the information processing apparatus according to supplementary note 1, wherein the selected feature determiner determines the selected features that minimize the submodular objective function.

(Supplementary Note 3)

There is provided the information processing apparatus according to supplementary note 1, wherein each feature included in the set of features includes a plurality of parameters.

(Supplementary Note 4)

There is provided the information processing apparatus according to supplementary note 1, 2, or 3, wherein the selected feature determiner optimizes the submodular objective function formed from a term using two features at maximum as arguments to determine the selected features.

(Supplementary Note 5)

There is provided the information processing apparatus according to any one of supplementary notes 1 to 4, wherein the relevance evaluator calculates the relevance using at least two features as arguments.

(Supplementary Note 6)

There is provided the information processing apparatus according to any one of supplementary notes 1 to 5, wherein the relevance evaluator calculates the relevance using a Fisher score.

(Supplementary Note 7)

There is provided the information processing apparatus according to any one of supplementary notes 1 to 6, wherein the redundancy evaluator calculates the redundancy from two features extracted from the set of features.

(Supplementary Note 8)

There is provided the information processing apparatus according to any one of supplementary notes 1 to 7, wherein the selected feature determiner optimizes, by graph cut, an objective function including the relevance calculated by the relevance evaluator and the redundancy calculated by the redundancy evaluator.

(Supplementary Note 9)

There is provided an information processing method comprising:

evaluating relevance of each feature included in a set of features;

evaluating redundancy between the features included in the set of features; and determining selected features such that a submodular objective function defined using the relevance calculated in the evaluating the relevance and the redundancy calculated in the evaluating the redundancy meets a predetermined condition.

(Supplementary Note 10)

There is provided a non-transitory computer-readable storage medium storing an information processing program that causes a computer to execute:

evaluating relevance of each feature included in a set of features;

evaluating redundancy between the features included in the set of features; and determining selected features such that a submodular objective function defined using the relevance calculated in the evaluating the relevance and the redundancy calculated in the evaluating the redundancy meets a predetermined condition.

This application is based upon and claims the benefit of priority from Japanese patent application No. 2011-031856, filed on Feb. 17, 2011, the disclosure of which is incorporated herein in its entirety by reference.

The invention claimed is:

1. An information processing apparatus comprising: a processor configured to execute:

a relevance evaluator that evaluates relevance $E_1$ by calculating relevance of each feature $S_i$ included in a set of features by $E_1$ ($s_i$, $X^{(i)}$, y), where $S_i$ indicates selection or non-selection of the feature, $X^{(i)}$ is the sample group including only the $i^{th}$ feature, and y is class level;

a redundancy evaluator that evaluates redundancy $E_2$ by calculating redundancy between the features included in the set of features by $E_2(s_i, s_j, X^{(i)}, X^{(j)}, y)$, wherein $S_j$ indicates selection or non-selection of the feature, $X^{(j)}$ is the sample group including only the $j^{th}$ feature and the redundancy E2 satisfies a submodularity represented by $$E_2(0,0,X^{(i)},X^{(j)},y)+E_2(1,1,X^{(i)},X^{(j)},y) \leq E_2(0,1,X^{(i)},X^{(j)},y)+E_2(1,0,X^{(i)},X^{(j)},y); \text{ and}$$

a selected feature determiner that determines selected features that minimize a submodular objective function E defined as a sum of the relevance $E_1$ calculated by said relevance evaluator and the redundancy $E_2$ calculated by said redundancy evaluator wherein the submodular objective function E defined by $$E(s) = -\sum_i E_1(s_i, X^{(i)}, y) + \lambda \sum_{i,j} E_2(s_i, s_j, X^{(i)}, X^{(j)}, y)$$

where $\lambda$ is a positive constant that determines a relative weight of two terms corresponding to the $i^{th}$ feature and the $j^{th}$ feature.

2. The information processing apparatus according to claim 1, wherein each feature included in the set of features includes a plurality of parameters.

3. The information processing apparatus according to claim 1, wherein said selected feature determiner optimizes the submodular objective function formed from a term using two features at maximum as arguments to determine the selected features.

4. The information processing apparatus according to claim 1, wherein said relevance evaluator calculates the relevance using at least two features as arguments.

5. The information processing apparatus according to claim 1, wherein said relevance evaluator calculates the relevance using a Fisher score.

6. The information processing apparatus according to claim 1, wherein said redundancy evaluator calculates the redundancy from two features extracted from the set of features.

7. The information processing apparatus according to claim 1, wherein said selected feature determiner optimizes, by graph cut, an objective function including the relevance calculated by said relevance evaluator and the redundancy calculated by said redundancy evaluator.

8. The information processing apparatus according claim 1 wherein relevance $E_1$ is evaluated by using Fisher linear discriminant analysis, and, wherein the redundancy evaluator calculates the redundancy E2 using a coefficient $\rho$ of correlation by $$E_2(s_i, s_j, X^{(i)}, X^{(j)}, y) = \begin{cases} a_{00}|\rho_{ij}| & (s_i = 0, s_j = 0) \\ a_{01}|\rho_{ij}| & (s_i = 0, s_j = 1) \\ a_{10}|\rho_{ij}| & (s_i = 1, s_j = 0) \\ a_{11}|\rho_{ij}| & (s_i = 1, s_j = 1) \end{cases}$$

where $a_{00}+a_{11} \leq a_{01}+a_{10}$ and where $$\rho_{ij} = \frac{\sum_n (X_n^{(i)} - \overline{X^{(i)}})(X_n^{(j)} - \overline{X^{(j)}})}{\sqrt{\sum_n (X_n^{(i)} - \overline{X^{(i)}})^2} \sqrt{\sum_n (X_n^{(j)} - \overline{X^{(j)}})^2}}$$

9. An information processing method comprising:

evaluating relevance $E_1$ of each feature $S_i$ included in a set of features by $E_1$ ($s_i$, $X^{(i)}$, y), where $S_i$ indicates selection or non-selection of the feature, $X^{(i)}$ is a sample group including only the ith feature and y is a class level;

evaluating redundancy $E_2$ between the features included in the set of features by $E_2(s_i, s_j, X^{(i)}, X^{(j)}, y)$, wherein $S_j$ indicates selection or non-selection of the feature, $X^{(j)}$ is the sample group including only the $j^{th}$ feature and the redundancy E2 the redundancy E2 is defined to always meet a submodularity represented by $E_2(0,0,X^{(i)},X^{(j)},y)+E_2(1,1,X^{(i)},X^{(j)},y) \leq E_2(0,1,X^{(i)},X^{(j)},y)+E_2(1,0,X^{(i)},X^{(j)},y)$; and determining selected features that minimize a submodular objective function E defined as a sum of the relevance $E_1$ calculated in the evaluating the relevance and the redundancy $E_2$ calculated in the evaluating the redundancy, wherein the submodular objective function E defined by $$E(s) = -\sum_i E_1(s_i, X^{(i)}, y) + \lambda \sum_{i,j} E_2(s_i, s_j, X^{(i)}, X^{(j)}, y)$$

where $\lambda$ is a positive constant that determines the relative weight of two terms corresponding to the $i^{th}$ feature and the $j^{th}$ feature.

10. A non-transitory computer-readable storage medium storing an information processing program that causes a computer to execute:

evaluating relevance $E_1$ of each feature $S_i$ included in a set of features by $E_1$ ($s_i$, $X^{(i)}$, y), where $S_i$ indicates selection or non-selection of the feature, $X^{(i)}$ is a sample group including only the ith feature and y is a class level;

evaluating redundancy $E_2$ between the features included in the set of features by $E_2(s_i, s_j, X^{(i)}, X^{(j)}, y)$, wherein $S_j$ indicates selection or non-selection of the feature, $X^{(j)}$ is the sample group including only the $j^{th}$ feature and the redundancy E2 the redundancy E2 is defined to always meet a submodularity represented by $E_2(0,0,X^{(i)},X^{(j)},y)+E_2(1,1,X^{(i)},X^{(j)},y) \leq E_2(0,1,X^{(i)},X^{(j)},y)+E_2(1,0,X^{(i)},X^{(j)},y)$; and determining selected features that minimize a submodular objective function E defined as a sum of the relevance $E_1$ calculated in the evaluating the relevance and the redundancy $E_2$ calculated in the evaluating the redundancy, wherein the submodular objective function E defined by $$E(s) = -\sum_i E_1(s_i, X^{(i)}, y) + \lambda \sum_{i,j} E_2(s_i, s_j, X^{(i)}, X^{(j)}, y)$$

where $\lambda$ is a positive constant that determines the relative weight of two terms corresponding to the $i^{th}$ feature and the $j^{th}$ feature.

* * * * *